United States Patent [19]
Domb

[11] Patent Number: 4,997,904
[45] Date of Patent: Mar. 5, 1991

[54] AROMATIC POLYANHYDRIDE COMPOSITIONS

[75] Inventor: Abraham J. Domb, Baltimore, Md.

[73] Assignee: Nova Pharmaceutical Corporation, Baltimore, Md.

[21] Appl. No.: 399,222

[22] Filed: Aug. 25, 1989

[51] Int. Cl.$^5$ .............................................. C08G 63/18
[52] U.S. Cl. ..................................... 528/206; 528/207;
528/271; 528/274; 528/302; 528/303; 528/308;
528/308.6; 528/176; 424/78; 424/426
[58] Field of Search ............... 528/206, 207, 271, 274,
528/302, 308, 308.6, 176; 424/426, 78

[56] References Cited

U.S. PATENT DOCUMENTS

| | | | |
|---|---|---|---|
| 4,757,128 | 7/1988 | Domb et al. | 528/271 |
| 4,789,724 | 12/1988 | Domb et al. | 528/176 |
| 4,857,311 | 8/1989 | Domb et al. | 424/78 |
| 4,886,870 | 12/1989 | D'Amore et al. | 528/206 |
| 4,888,176 | 12/1989 | Langer et al. | 424/426 |
| 4,891,225 | 1/1990 | Langer et al. | 424/428 |
| 4,906,474 | 3/1990 | Langer et al. | 424/428 |
| 4,993,431 | 6/1990 | Domb et al. | 528/328 |

OTHER PUBLICATIONS

Domb and Langer, (1987) *J. Poly. Sci.* 25: 3373.
Leong, et al., (1985), *J. Biomed. Res.* 19: 941.
Domb and Langer (1989) *Macromolecules* 22: 2117.
Ron; et al., (1989) *Proceed. Inter. Control Rel. Bioact. Mater.* 16.
*Ency. of Poly. Sci. & Tech.* 10, 630 (1969).
Cottler and Matzner (1967) *Chemisch Weekblad* 63: 113–128.
Domb and Langer (1987) *J. Polym. Sci.* 25: 3373.
Yoda and Miyaka (1959) *Journal of Polymer Science:* 32 1120.
Mathiowitz, et al. (1988) *J. App. Poly. Sci.* 35: 755.
Domb and Langer (1988) *Macromolecules* 21: 1925.
Chasin, et al., (1988) *Bio Pharm. Manufact.* 1: 33–46.
Brem, et al. (1989) *W Sel. Cancer Ther.* 5: 55.
Mathiowitz, et al., (1989) *Proceed. Intern. Symp. Control Rel. Bioact. Mater.* 16: 161.

*Primary Examiner*—Morton Foelak
*Assistant Examiner*—Sam A. Acquah
*Attorney, Agent, or Firm*—Kilpatrick & Cody

[57] ABSTRACT

Aromatic anhydride copolymers containing at least two aromatic diacid units, which are soluble in chloroform or dichloromethane to concentrations between approximately 0.5 to 50% weight/volume, melt at temperatures below 180° C., and have low crystallinity are disclosed. The copolymers may contain between 0 and approximately 30% aliphatic diacid units. All copolymers are insoluble in carbon tetrachloride, i.e., less than 0.1% polymer by weight/volume solvent). The desired properties are the result of adding between 10 and 90% of a second aromatic diacid, to the copolymer composition which introduces irregularity in the polymer chains that dramatically alter the polymer properties, decreasing the crystallinity and melting point and increasing the solubility in the common solvents, dichloromethane or chloroform. An additional decrease in Tg and MP, with an increase in flexibility, is obtained by adding small amount of aliphatic diacid, up to about 30%.

13 Claims, 1 Drawing Sheet

AROMATIC POLYANHYDRIDE COMPOSITIONS

BACKGROUND OF THE INVENTION

This generally relates to biodegradable polymers useful for medical applications, especially polyanhydrides having improved physicochemical properties.

Polyanhydrides are particularly useful as controlled release devices since they are biocompatible and degrade linearly by hydrolysis. Polyanhydrides of aromatic diacids offer several advantages over aliphatic polymers. They possess longer release and degradation times when used as degradable materials for drug release (Leong, et al., *J. Biomed. Res.* 19, 941, (1985)), possess high thermodynamic stability in solid state and organic solutions (A. Domb and R. Langer, *Macromolecules*, 22, 2117, (1989)), and are more favorable with respect to drug-polymer interactions, especially for proteins (Ron, et al., *Proceed. Inter. Control Rel. Bioact. Mater.*, 16, (1989)). Aromatic and aliphatic diacids are acids where the carboxylic acid is connected to an aromatic ring or aliphatic residue, respectively.

Unfortunately, aromatic polyanhydrides have in general very low solubility in common organic solvents (less than 0.1% solubility in chlorinated, aromatic, or aliphatic hydrocarbons) and have high melting points, generally in excess of 200° C., *Encyclopedia of Polym. Sci. Tech.*, 10, 630 (1969) and references within). These properties limit the uses of aromatic polymers since they cannot be fabricated by either solvent techniques (fabrication into films or microspheres from solvents) due to their low solubility, nor using melt processing techniques due to their high melting point. Aromatic polymers are also usually highly crystalline, with the result that the polymers are characterized by brittleness and poor flexibility.

One way to overcome these limitations is by copolymerization of aromatic diacids with aliphatic diacids. The resulting copolymers have relatively low melting points, and increased mechanical strength as the aromatic content is increased (A. Domb and R. Langer, *J. Polym. Sci.* 25, 3373 (1987)). However, these copolymers also have the disadvantages of aliphatic polymers, e.g. hydrolytic and thermal instability, and copolymers containing more than 65% aromatic diacids are insoluble in common organic solvents and have high crystallinity and melting points.

Very little has been reported on the synthesis and properties of copolymers of aromatic diacids. Cottler and Matzner, reported in *Chemich Weekblad*, 63, 113 (1967), that insoluble copolymers of terephthalic and isophthalic acids had melting points in the range of 250° to 315° C. Several copolymers of terephthalic acid or isophthalic acid and nitrogen containing aromatic diacids were also reported that melted at temperatures above 200° C., and were reported to be "soluble" in carbon tetrachloride, although no definition of the percent of solubility was given. There are no reports of a fully aromatic or even a copolymer of aromatic and aliphatic diacids of more than 70% aromaticity, which is soluble in chloroform or dichloromethane, has low crystallinity, and melts at a temperature below 200° C.

The ideal polyanhydride would be one which possesses the properties of an aromatic polymer, good hydrolytic and thermodynamic stability and superior mechanical strength, yet is soluble in common organic solvents and melts at temperature below 200° C.

It is therefore an object of the present invention to provide polyanhydride compositions with high aromatic content, of at least 70% aromatic diacid units, which are soluble in organic solvents such as dichloromethane or chloroform, melt at temperatures below 200° C., and have low crystallinity.

It is another object of the present invention to provide polyanhydride compositions with high aromatic content which can be formulated into films or microspheres using solvent techniques, or which can be formulated into filaments or films by melt techniques for biomedical use.

SUMMARY OF THE INVENTION

Aromatic anhydride copolymers containing at least two aromatic diacid units, which are soluble in chloroform or dichloromethane to concentrations between approximately 0.5 to 50% weight/volume, melt at temperatures below 180° C., and have low crystallinity, are disclosed. The copolymers may contain between 0 and approximately 30% aliphatic diacid units. All copolymers are insoluble in carbon tetrachloride, i.e., less than 0.1% polymer by weight/volume solvent). The desired properties are the result of adding between 10 and 90% of a second aromatic diacid to the copolymer composition which introduces irregularity in the polymer chains. The irregularities in the chains dramatically alter the polymer properties, decreasing the crystallinity and melting point and increasing the solubility in the common organic solvents, dichloromethane or chloroform. By adding a small amount of aliphatic diacid, up to about 30 mole %, an additional decrease in Tg and MP, with increase in flexibility, is obtained.

Examples demonstrating the properties of these polymers include copolymers polymerized from isophthalic acid, terephthalic acid, 1,3 bis (p-carboxyphenoxypropane), fumaric acid, adipic acid, sebacic acid, and 1,10 dodecanedioic acid. Fumaric acid was included among the aromatic monomers because of its similar properties to aromatic polymers. The preferred copolymers are polymerized from diacids having the general formulas

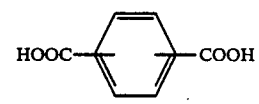

and

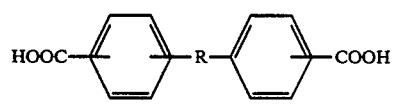

in which R is a divalent organic radical group. Examples of such diacids include isophthalic acid, terephthalic acid, bis(carboxyphenoxyalkanes), bis(carboxyphenylalkanes), and their ring substitution derivatives.

DETAILED DESCRIPTION OF THE INVENTION

Figure 1:
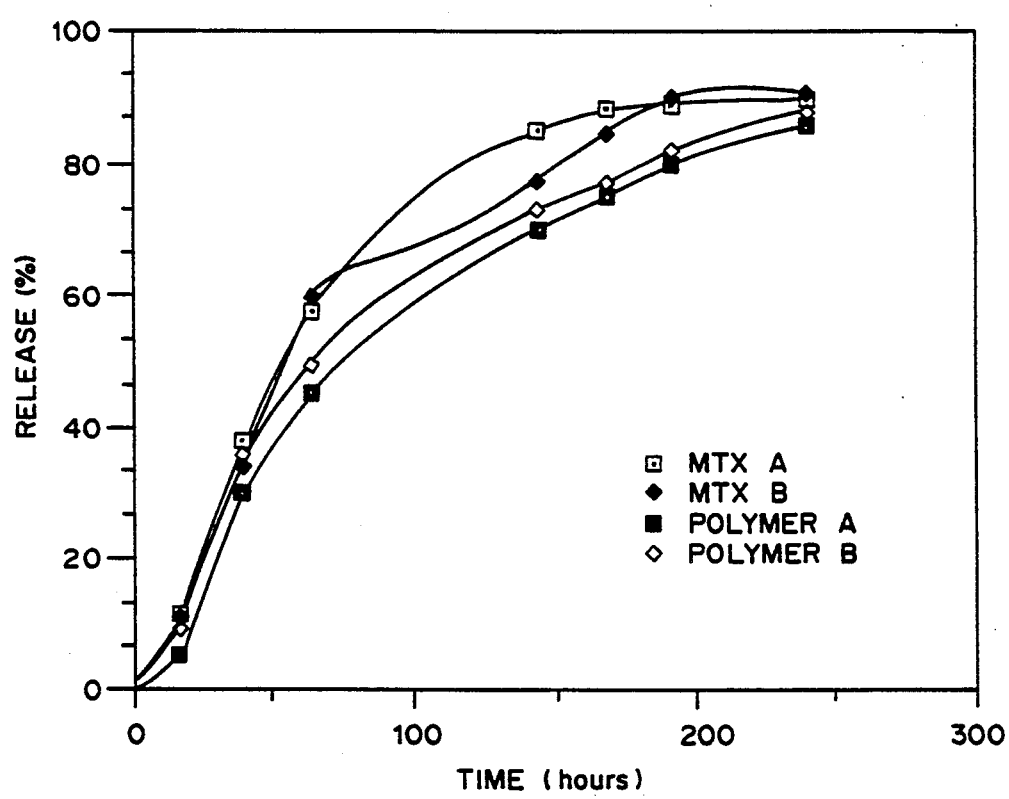
FIG. 1 is a graph of the percent release of methotrexate (MTX) from aromatic copolymer and degradation of polymer over time in hours. [ ] is release of MTX from polymer A; dark < > is release of MTX from polymer B; dark [ ] is degradation of polymer A; and < > is degradation of polymer B.

The present invention is further described with reference to the following non-limiting examples. For comparative purposes, the thermal and solubility properties of the aromatic homopolymers and copolymers with aliphatic diacids made of the selected diacids, is described in Table 1. This table shows that the aromatic homopolymers and copolymers with up to about 35% aliphatic diacid of the selected diacids are crystalline, have high melting points, and are insoluble in dichloromethane, chloroform, carbon tetrachloride, or tetrahydofuran (THF).

In the following examples, polyanhydrides were prepared using diacids which are fully aromatic or contain less than 30% aliphatic diacid, yet melt at temperatures below 200° C., have low degrees of crystallinity, and are very soluble in dichloromethane or chloroform. This was achieved by adding 10 to 90% of a second aromatic diacid to the copolymer composition. The second aromatic diacid introduces irregularity in the polymer chains which dramatically change the polymer properties, the crystallinity and melting points, and the solubility in the common solvents, dichloromethane or chloroform. By adding up to about 30 mole % of aliphatic diacid, an additional decrease in transition glass temperature (Tg) and melting point (MP), with an increase in flexibility, is obtained.

TABLE 1

Physical properties of aromatic homopolymers.

| Polymer[a] | Melt. Point[b] °C. | Crystallinity | Solubility[c] | Ref.[d] |
|---|---|---|---|---|
| TA | 410 | crystalline | insoluble | 1,3 |
| TA-SA 51:49 | 280 | crystalline | insoluble | 1,3 |
| TA-SA 68:32 | 335 | crystalline | insoluble | 1,3 |
| TA-AA50:50 | 275 | crystalline | insoluble | 1,3 |
| TA-AA60:40 | 310 | crystalline | insoluble | 1,3 |
| P(CPP) | 256 | crystalline (53%) | insoluble | 2,3 |
| P(CPP-SA)70:30 | 203 | crystalline | insoluble | 3 |
| P(ISO) | 248 | crystalline | insoluble | 3 |
| P(ISO-SA)70:30 | 203 | crystalline | insoluble | 3 |
| P(ISO-DD)70:30 | 225 | crystalline | insoluble | 3 |
| P(FA) | 246 | crystalline | insoluble | 3 |
| P(FA-SA)70:30 | 148 | crystalline | insoluble | 3 |
| P(CPP-SA)20:80[e] | 66 | crystalline | soluble | 2,3 |
| P(ISO-SA)20:80 | 67 | crystalline | soluble | 3 |
| P(ISO-SA)35:65 | 47 | crystalline | soluble | 3 |
| P(ISO-SA)50:50 | 34 | amorphous | soluble | 3 |

[a]Isophthalic acid (ISO), terephthalic acid (TA), fumaric acid (FA), carboxyphenoxypropane (CPP), sebacic acid (SA), dodecanedioic acid (DD), adipic acid (AA).
[b]Determined by DSC, peak temperature was given as the melting point.
[c]Insoluble (less than 0.1% W/V) in dichloromethane, chloroform, carbon tetrachloride, or THF.
[d]References: 1. Yoda, N. and Miyaka, A. J. Polym. Sci. 32, 1120, (1959). 2. Mathiowitz, E., Saltzman, A. Domb, A., Dor, Ph. J. App. Poly. Sci. 35, 755 (1988). 3. As in examples.
[e]Copolymers with aliphatic diacids were added to the table for comparison.

Experimental

Instrumental and methods

Infrared spectroscopy was performed on a perkin-Elmer 1310 spectrophotometer (Perkin Elmer, CT.). Polymeric samples were film cast onto NaCl plates from a solution of the polymer in chloroform. Acids and prepolymer samples were either pressed into KBr pellets or dispersed in nujul onto NaCl plates. The melting points of acids and prepolymers were determined on a digital melting point apparatus (Electrothermal IA8100). Thermal properties of polymers were determined by a Differential scanning Calorimeter (DSC 7, Perkin Elmer, CT). The samples (4–6 mg) were analyzed at a 10° C./min heating rate in a nitrogen atmosphere. The Tg and melting temperature of the polymers were verified by observation of polymer changes when heating a polymer sample under pressure on a micro-melting point apparatus (Bristoline). The molecular weights of the polymers were estimated on a Waters GPC system (Waters, MA) consisting of a Waters 510 pump and Waters programmable multiwavelength detector at 254 nm wavelength. Samples were eluted in dichloromethane through two Styrogel TM columns (Waters, Linear and a $10^4$ A pore sizes) in series at a flow rate of 1.0 mL/min. Molecular weights of polymers were determined relative to polystyrene standards (Polysciences, PA, molecular weight range, 400 to 1,500,000) using Maxima 820 computer programs (Waters, MA.). Viscosity of polymers were determined on a Cannon 50 Ubelouhde viscosimeter (Cannon, PA) at 25° C. $^1H$ NMR spectra were obtained on a Varian 250 MHz spectrophotometer using chloroform-$d_1$ containing tetramethylsilane (TMS) as solvent for polymers and prepolymers. UV absorbencies were determined on a Lambda 3B spectrophotometer (Perkin Elmer, CT). Degradation studies were performed at 37° C., using compression molded or film cast discs of 200 mg polymer containing 5% W/W p-nitroaniline, placed in 200 ml solution of phosphate buffer pH 7.40. Drug release and degradation rates were determined from the UV absorption of the degradation products in the degradation solution.

Polymer synthesis

Purification of diacids

Iso-phthalic acid (ISO) and terephthalic acid (TA) were extracted with an acetone-water (1:1) mixture for 24 hours at room temperature, and Soxslet extracted with ethanol for 12 hours. 1,3-bis-carboxyphenoxypropane (CPP) was synthesized and purified as described by A. J. Domb and R. Langer, J. Poly. Sci. 25, 3373 (1987). Fumaric acid (FA) was recrystallized from water. Sebacic acid (SA), 1,10 dodecanedioic acid (DD), and adipic acid (AA) were recrystallized from ethanol. All acid monomers were dried in a dry desiccator under vacuum for 48 hours before use.

Preparation of prepolymers

Iso-phthalic acid prepolymer was prepared as follows: 50 g of the acid powder was added to 500 ml refluxing acetic anhydride with constant stirring. After 10 min under reflux, most of the powder was dissolved and the reaction mixture was removed from the heat bath and filtered. The solution was evaporated to dryness using an evaporator equipped with a vacuum pump and a water bath at 65° C. The remaining liquid was mixed with 20 ml of dry toluene and left to crystallize at room temperature for 24 hours. The white precipitate was filtered and extracted with 200 ml diethyl ether for 12 hours, to yield 40 g of prepolymer. MP 105°–120° C., IR (film cast, $CM^{-1}$) 1790 (s,s), 1720 (s,s), 1600 (s,w), 1H-NMR (CDCl3,ppm) 8.7 (d, 1H); 8.3 (m, 2H); 7.6 (t, 1H); 2.4 (s, 6H), molecular weight (GPC) narrow peak $Mn=580$, $Mw=820$.

Terephthalic acid prepolymers prepared under similar conditions had a high melting point product (>300° C.) which is not useful for polymerization at 180° C.

Isophthalic-terephthalic acids (80:20 and 75:25 molar ratio), terephthalic acid-fumaric acid (45:55 molar ratio), terephthalic acid-CPP (45:55 molar ratio), and terephthalic acid-sebacic acid (30:70 molar ratio) mixed prepolymers were prepared by reacting 50 g of the mixture of acids in 500 ml refluxing acetic anhydride for 10 min and isolated as above. The mixed prepolymers were purified by recrystallization from toluene solution. Isophthalic-terephthalic acids mixed prepolymer (80:20), MP 90°-120° C., IR (film cast, $CM^{-1}$) 1790 (s,s), 1600 (s,w). (GPC) narrow peak Mn=640, Mw=910. Terephthalic acid-fumaric acid mixed prepolymer (45:55), MP 80°-85° C., IR (film cast, $CM^{-1}$) 1790 (s,s), 1720 (s,s), 1600 (s,w). (GPC) narrow peak, Mn=540, Mw=850. Terephthalic acid-CPP mixed prepolymer (30:70), MP 105°-120°C., IR (film cast, $CM^{-1}$) 1790 (s,s), 1720 (s,s), 1600 (s,w). (GPC) narrow single peak, Mn=720, Mw=1050).

CPP, fumaric acid, and aliphatic acid prepolymers were prepared as described by A. J. Domb and R. Langer, *J. Poly. Sci.*, 25:3373 (1987).

Polymerization

Polymers were synthesized by condensation polymerization of the prepolymers at 180° C. for 90 min under high vacuum (greater than 100 mm Hg) as described by A. J. Domb and R. Langer, *J. Poly. Sci.*, 25, 3373 (1987). At the end of the polymerizations a viscous melt was obtained. Copolymers with terephthalic acid were synthesized from the corresponding mixed prepolymers. Polymers can also be synthesized by solution polymerization as described by A. J. Domb, E. Ron, and R. Langer, *Macromolecules*, 21, 1925 (1988). The molecular weight and the physical properties are described in tables 2 and 3. When catalyst was used, 2 weight % of finely powdered cadmium acetate dihydrate was mixed with the prepolymers and the prepolymers polymerized.

The prepolymers of CPP, fumaric acid, isophthalic acid, and aliphatic acids melted at low temperatures, however, the prepolymer of terephthalic acid melted at a temperature above 200° C. and was not useful for polymerization at 180° C. To overcome this problem, mixed prepolymers of terephthalic acid with CPP, isophthalic acid, fumaric acid, and sebacic acid were prepared which melted at temperatures below 120° C. The mixed prepolymers (dicarboxylic acid diacetyl anhydride) were purified successfully by recrystallization from toluene. The molecular weight properties of the polymers are summarized in Table 2. Weight average molecular weights of up to 40,000 were obtained. Incorporation of an aliphatic diacid yielded polymers with higher molecular weight. Polymerization in the presence of a coordinative catalyst, such as cadmium acetate, increased the polymerization rate with a slight increase in molecular weight (Table 3).

TABLE 2

Molecular Weights of Aromatic copolymers[a]

| Polymer[b] | Molecular Weight Mn | Molecular Weight Mw | Viscosity dl/g |
|---|---|---|---|
| P(CPP-ISO)20:80 | 13,700 | 34,500 | 0.41 |
| P(CPP-ISO)50:50 | 12,800 | 31,600 | 0.39 |
| P(CPP-ISO-TA)50:40:10 | 10,700 | 25,200 | 0.34 |
| P(CPP-ISO-TA)25:60:15 | 12,500 | 27,800 | 0.35 |
| P(TA-ISO)25:75 | 8,600 | 22,400 | 0.34 |
| P(TA-ISO)20:80 | 10,200 | 24,700 | 0.35 |
| P(ISO-FA)75:25 | 8,100 | 19,500 | 0.31 |
| P(ISO-FA)50:50 | 7,400 | 16,100 | 0.28 |
| P(ISO-FA)25:75 | 6,600 | 14,500 | 0.25 |
| P(ISO-FA)80:20 | 7,800 | 17,300 | 0.28 |
| P(CPP-FA)35:65 | 7,200 | 14,800 | 0.24 |
| P(FA-TA-ISO)55:9:36 | 6,600 | 15,400 | 0.23 |
| P(FA-TA-SA)56:16:28 | 7,900 | 16,300 | 0.23 |
| P(FA-CPP-SA)55:25:20 | 8,200 | 15,900 | 0.22 |
| P(TA-CPP-SA)24:48:28 | 12,700 | 31,800 | 0.36 |
| P(CPP-ISO-SA)15:58:27 | 14,600 | 39,700 | 0.37 |
| P(CPP-ISO-SA)17:66:16 | 15,200 | 36,100 | 0.38 |
| P(CPP-ISO-AA)17:66:16 | 6,000 | 15,600 | 0.22 |
| P(CPP-ISO-DD)17:66:16 | 13,400 | 28,600 | 0.35 |
| P(TA-ISO-SA)17:66:16 | 10,800 | 27,500 | 0.34 |

[a]Molecular weights were estimated by GPC, viscosity was measured in dichloromethane at 25° C.
[b]Isophthalic acid (ISO), terephthalic acid (TA), fumaric acid (FA), carboxyphenoxypropane (CPP), sebacic acid (SA), dodecanedioic acid (DD), adipic acid (AA).

TABLE 3

Cadmium Acetate catalysis in the polymerization of aromatic copolymers[a]

| Reaction Time (min) | No Catalyst Mw | No Catalyst Mn | With Catalyst[b] Mw | With Catalyst[b] Mn |
|---|---|---|---|---|
| 20 | 11,200 | 5,600 | 24,300 | 11,600 |
| 40 | 14,800 | 7,800 | 24,800 | 12,200 |
| 60 | 17,400 | 7,900 | 24,400 | 12,300 |
| 90 | 18,700 | 8,970 | 25,100 | 12,100 |

[a]Mixture of CPP and Isophthalic acid prepolymers (20:80 molar ratio), polymerized at 180° C. under vacuum of 200 mm Hg. Molecular weight was determined by GPC.
[b]2% w/w of cadmium acetate dihydrate was mixed with the prepolymers and polymerized.

Solubility test 10 mg of polymer powder was added to 10 ml of solvent (0.1% W/V) and left to dissolve for 2 hours at room temperature with constant stirring. The solubility was determined when the polymer completely dissolved in solution. Polymers that were soluble were tested for high solubility by dissolving 0.75 g of polymer in 5 ml of solvent (15% W/V). The solubility of the polymers in dichloromethane, chloroform, carbon tetrachloride, tetrahydrofuran (THF), Toluene, hexanes, and diethyl ether, was then determined.

Solubility of polymers is a major factor on their uses and applications. For polyanhydrides to be suitable for controlled release applications, it is essential that the polymers be soluble in common organic solvents, so they can be fabricated into microspheres, films, coatings, or fibers by drawing from solvent. The most commonly used organic solvents for controlled release fabrications are dichloromethane and chloroform. These are volatile, non-flammable and inexpensive solvents that can be completely removed from the product by vacuum.

Only little data is available concerning the solubility of polyanhydrides. The data given in the literature is general and not quantitative and not defined, i.e., the term "soluble" can mean 0.1% W/V or 10% W/V. As used herein, "soluble" is defined as greater than 0.2% W/V polymer in solution, and "practically soluble" as more than 0.5% W/V, since lower solubilities are impractical for fabrication purposes. "Very soluble" is defined as greater than 15% W/V. Aromatic and heterocyclic polymers show very low solubility. Aliphatic polyanhydrides of the structure, $HOOC\text{-}(CH_2)_n\text{-}COOH$, are soluble in dichloromethane and chloroform. Copolymers of aliphatic and aromatic diacids are also, in general, soluble in dichloromethane and chloroform, however the solubility decreases with the increase in the aromatic content, and polymers containing more than 60% aromatic acids are insoluble, as shown in Table 1. The most widely used solvent for polyanhydrides is m-cresol. In some cases other solvents have been used, such as phenol, nitrobenzene, dimethyl formamide, a-methyl naphthalene, biphenyl and diphenyl ether but these solvents are not useful for fabrication purposes.

ing point apparatus. These data indicate these are amorphous polymers with very low crystallinity. X-ray diffraction of several samples verified very low crystallinity of 5% or less.

All polymers in tables 4 and 5 were insoluble in carbon tetrachloride, tetrahydrofuran (THF), toluene, hexanes, and diethyl ether. In the case of THF the polymer became gummy and sticky but was not completely dissolved. All were very soluble, greater than 15% W/V, in dichloromethane or chloroform.

TABLE 4

Thermal and solubility properties of aromatic copolyanhydrides

| Polymer[a] | Transition[b] Temp. °C. | Onset | Heat cap. J/qm | Solubility |
|---|---|---|---|---|
| P(CPP-ISO)20:80 | 110 | 103(Tg) | 2.59 | ++ |
| P(CPP-ISO)50:50 | 100 | 93(Tg) | 3.50 | ++ |
| P(CPP-ISO)75:25 | 230 | 215 | | − |
| P(CPP-ISO-TA) 50:40:10 | 111.6 | 93(Tg) | 2.54 | ++ |
| P(CPP-ISO-TA) 25:60:15 | 105 | 98(Tg) | 2.33 | ++ |
| P(TA-ISO)25:75 | 124 | 117(Tg) | 1.41 | ++ |
| P(TA-ISO)20:80 | 110 | 103(Tg) | 1.06 | ++ |
| P(ISO-FA)75:25 | 125 85 240 DECOMPOSITION | 120 79(Tg) | 0.37 | ++ |
| P(ISO-FA)50:50 | 75 230 DECOMPOSITION | 70 | 0.84 | ++ |
| P(ISO-FA)25:75 | 68 215 DECOMPOSITION | 60 | 4.17 | + |
| P(ISO-FA)80:20 | 100 237 DECOMPOSITION | 92 | 2.1 | ++ |
| P(CPP-FA)35:65 | 72 190 DECOMPOSITION | 62 | 0.9 | ++ |
| P(FA-TA-ISO)55:36:9 | 68 210 DECOMPOSITION | 58 | 3.1 | ++ |

[a]Isophthalic acid (ISO), terephthalic acid (TA), fumaric acid (FA), carboxyphenoxypropane (CPP).
[b]Transition temperature (Tg) was determined by DSC, and verified by melting under pressure. No melting point was recognized up to 250° C., except in the case of decomposition. All polymers melted to a viscous melt at a temperature below 180° C., and were amorphous solids.

In the foregoing examples the solubility of the polymers has been tested in dichloromethane, chloroform, carbon tetrachloride, tetrahydrofuran (THF), toluene, hexanes, and diethyl ether.

Thermal analysis

Generally aliphatic polyanhydrides with a straight chain melt at low temperatures, usually between 60° and 120° C. with Tg below room temperature, and possess high crystallinity levels, greater than 50%. Aromatic polyanhydrides melt at much higher temperatures, above 200° C., and possess high crystallinity, above 50%. Introduction of aliphatic comonomers decreases the crystallinity and melting point, as reported by Ron, et al., Proceed. Inter. Control. Rel. Bioact. Mater., 15, (1988).

The present examples are the first demonstration that a dramatic decrease in Tg, melt temperature, and crystallinity can be achieved by copolymerization of at least two aromatic diacid units. A further decrease in Tg and melt temperature, with improvement in mechanical properties, can be obtained by adding small amounts of aliphatic diacids, to between approximately one and 30 mole %. Only one transition temperature was recognized in DSC chromatogram, which is probably the glass transition temperature (Tg). No melting peak was recognized although all polymers were melted to a viscous melt at 180° C., as observed in the micro-melt- Spectral analysis of polymers IR analysis Samples for analysis were prepared by film casting onto NaCl pallets from dichloromethane solution. Fully aromatic copolymers are characterized by the following absorbencies:

3070 cm$^{-1}$—medium sharp single peak (unsaturated C—H stretchings);

1790 cm$^{-1}$—strong sharp single peak (aromatic anhydride bond);

1720 cm$^{-1}$—strong sharp single peak (aromatic anhydride bond);

1600 cm$^{-1}$—strong sharp single peak (aromatic ring).

Polymers containing aliphatic residues e.g.: CPP, or aliphatic diacids, show absorbencies at 2920 cm$^{-1}$ (strong sharp peak) with a shoulder at 2840 cm$^{-1}$, characteristic for aliphatic methylene units.

1H-NMR analysis

The 1H-NMR analysis of the 20:80 and 50:50 copolymers of CPP and isophthalic acid is as follows:

20:80 copolymer: (CDCl3,ppm) 8.4 (s,4H), 7.9 (s,8H), 7.6 (s,4H), 7.2 (s,4H), 6.5 (m,4H), 3.8 (s,4H), 1.9 (m,2H).

50:50 copolymer: (CDCl3,ppm) 8.4 (s,1H), 7.9 (s,2H), 7.6 (s,4H), 7 2 (s,1H), 6.5 (m,4H), 3.8 (s,4H), 1.9 (m,2H).

TABLE 5
Aromatic polymers containing aliphatic diacid

| polymer[a] | Transition temp. °C. | Onset | Heat cap. J/gm | Solubility[b] |
|---|---|---|---|---|
| FA/TA/SA 56:16:28 | 93.2 | 85 | 2.97 | ++ |
|  | 47(Tg) | 41 | 0.6 |  |
|  | 215 decomposition |  |  |  |
| FA/CPP/SA 55:25:20 | 46(Tg) | 40 | 0.2 | ++ |
|  | 200 decomposition |  |  |  |
| TA/CPP/SA 24:48:28 | 153 | 124 | 6.7 | ++ |
|  | 42(Tg) | 36 | 0.4 |  |
| CPP-ISO-SA 15:58:27 | 46(Tg) | 38 | 3.07 | ++ |
| CPP/ISO.SA 17:66:16 | 83 | 77 | 0.4 | ++ |
|  | 45(Tg) | 41 | 0.3 |  |
| CPP/ISO/AA 17:66:16 | 43(Tg) | 38 | 0.8 | ++ |
| CPP/ISO/DD 17:66:16 | 76(Tg) | 75 | 2.1 | ++ |
| TA/ISO/SA 17:66:16 | 136 | 133 | 0.2 | ++ |
|  | 43(Tg) | 40 | 0.2 |  |

[a]Isophthalic acid (ISO), terephthalic acid (TA), fumaric acid (FA), carboxyphenoxypropane (CPP), sebacic acid (SA), dodecanedioic acid (DD), adipic acid (AA).
[b]Polymers were very soluble (++) in dichloromethane and chloroform, but insoluble in carbon tetrachloride or THF.

Mechanical properties

All polymers in tables 2 and 3 show excellent film forming properties when cast from solution, and form strong and flexible fibers when drawn from the melt.

Stability in solid state

Samples of P(CPP-ISO) 20:80, P(CPP-ISO)50:50, and P(TA-ISO)20:80 were stored in glass containers under vacuum, at 5 and 25° C. for 40 days. The molecular weight of the polymers did not change at either storage temperatures.

Release and Degradation

Fine powder of MTX (100 mg) was dispersed in 5 ml of a dichloromethane solution containing either one gram of Poly(CPP-ISO)20:80 [polymer A] or poly(CPP-ISO-SA)14:58:28 [polymer B], and cast into a 5 cm diameter Teflon TM coated petri dish. After solvent evaporation at room temperature for 10 hours, a film 0.5 mm thick was obtained.

Samples of 200 mg films were placed in 20 ml 0.1M phosphate buffer pH 7.4 at 37° C. The solution was periodically replaced with fresh buffer solution, and analyzed for MTX by HPLC (C18 column, mobil phase: mixture of 0.01M ammonium formate, pH 3.5 solution and acetonitrile 80:20 v/v, detector UV at 308 nm for MTX and at 248 nm for degradation products). The results are summarized in FIG. 1.

The release rate of MTX is close to the degradation rate of the polymers. After 10 days, 85% of the drug was released and the polymer degraded. Both polymers showed similar results.

Biocompatibility of the Polymers 12 female Sprague-Dawley rats, 200–400 gram weight, 8–14 weeks of age were each implanted with a 200 mg compression molded disc of polymer as follows. After prepping and sterilely draping, a 8 cm midline incision was made on the dorsum of each rat. Using the tissue scissors, a pocket area was created 6 cm away from the midline incision. One 200 mg disc or no disc was implanted, and the wound was then closed using surgical clips. Three polymers were studied: poly(CPP-ISO)20:80, poly(CPP-ISO-SA)15:58:27, and clinical grade poly(CPP-SA)20:80 as reference. Control animals were not implanted with polymer. 7 days post implantation the rats were sacrificed and the site of implantation was examined.

Group 1: Control animals, 3/3 were normal, no swelling or redness.
Group 2: Poly(CPP-SA)20:80, ⅔ were normal, ⅓ showed red foci in site of implantation.
Group 3: Poly(CPP-ISO-SA)15:58:27, ⅔ were normal, ⅓ showed red foci in site o implantation.
Group 4: Poly(CPP-ISO)20:80, ⅔ were normal, ⅓ showed red foci and thickening in site of implantation.

Both aromatic copolymers displayed similar biocompatability to the poly(CPP-SA)20:80 reference, which is considered to be biocompatible.

Modifications and variations of the aromatic polyanhydrides of the present invention, and methods for preparation and use thereof, will be obvious to those skilled in the art from the foregoing detailed description of the invention. Such modifications and variations are intended to come within the scope of the appended claims.

I claim:

1. Anhydride copolymers comprising at least two different aromatic diacid units in a molar ratio of between approximately 10:90 and 90:10, whereby said copolymers are soluble in chloroform and dichloromethane, melt at a temperature below 200° C., and possess low crystallinity.

2. The anhydride copolymers of claim 1 wherein at least 70% of the diacid units are aromatic diacid units and the remainder are aliphatic diacid units.

3. The anhydride copolymers of claim 1 having less than about 5% crystallinity.

4. The anhydride copolymers of claim 1 polymerized from diacids selected from the group consisting of

and

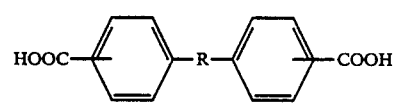

wherein R is a divalent organic radical group

5. The anhydride copolymers of claim 4 polymerized from diacids selected from the group consisting of isophthalic acid, terephthalic acid, bis(carboxyphenoxyalkanes), bis(carboxyphenylalkanes), and their ring substitution derivatives.

6. A method for making anhydride copolymers comprising:
polymerizing at least two different aromatic diacid units in a molar ratio of between approximately 10:90 and 90:10 to form copolymers soluble in chloroform and dichloromethane, melting at a temperature below 200° C., and possessing low crystallinity.

7. The method for making anhydride copolymers of claim 6 wherein at least 70% of the diacid units are aromatic diacid units and the remainder are aliphatic diacid units.

8. The method for making anhydride copolymers of claim 6 comprising reacting diacids of the formula:

and

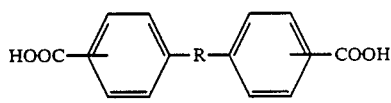

wherein R is a divalent organic radical group.

9. The method for making anhydride copolymers of claim 8 wherein the aromatic diacids are selected from the group consisting of isophthalic acid, terephthalic acid, bis(carboxyphenoxyalkanes), bis(carboxyphenylalkanes) and their ring substitution derivatives.

10. The method for making anhydride copolymers of claim 6 wherein said polymerization reaction is effected by first reacting said diacids with acetic anhydride to form dicarboxylic acid diacetyl anhydride prepolymers and then polymerizing the prepolymers in the presence of a coordinative catalyst to form the copolymers.

11. The method of claim 6 further comprising preparing drug delivery implants by dissolving the copolymer in an organic solvent selected from the group consisting of chloroform and dichloromethane, casting the polymer solution, and removing the solvent from the polymer.

12. The method of claim 6 further comprising preparing drug delivery implants by melting the copolymer at a temperature of less than 200° C.

13. A polymer solution comprising between approximately 0.5 and 50% weight/volume of an anhydride copolymer of at least two different aromatic diacids in a molar ratio of between approximately 10 and 90 in an organic solvent selected from the group consisting of chloroform and dichloromethane.

* * * * *

UNITED STATES PATENT AND TRADEMARK OFFICE
CERTIFICATE OF CORRECTION

PATENT NO. : 4,997,904
DATED : Mar. 5, 1991
INVENTOR(S) : Abraham J. Domb

It is certified that error appears in the above-identified patent and that said Letters Patent is hereby corrected as shown below:

Col. 3, line 60: Capitalize "P" in "perkin".
Col. 4, line 12: Replace "Styrogel TM" with —Styrogel$^{TM}$—.
Col. 8, line 67: Replace "7 2" with —7.2—.
Col. 9, line 40: Replace "Teflon TM" with —Teflon$^{TM}$—.
Col. 10, line 28: After "site" replace "o" with —of—.

Signed and Sealed this

Eighth Day of November, 1994

Attest:

BRUCE LEHMAN

Attesting Officer  Commissioner of Patents and Trademarks